(12) United States Patent
Burkholz et al.

(10) Patent No.: US 11,173,277 B2
(45) Date of Patent: Nov. 16, 2021

(54) MULTI-DIAMETER CATHETER AND RELATED DEVICES AND METHODS

(71) Applicant: Becton, Dickinson and Company, Franklin Lakes, NJ (US)

(72) Inventors: Jonathan Karl Burkholz, Salt Lake City, UT (US); Joseph Spataro, Cottonwood Heights, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 275 days.

(21) Appl. No.: 16/037,319

(22) Filed: Jul. 17, 2018

(65) Prior Publication Data

US 2019/0321590 A1    Oct. 24, 2019

Related U.S. Application Data

(63) Continuation of application No. 62/660,646, filed on Apr. 20, 2018.

(51) Int. Cl.
*A61M 25/00* (2006.01)
*A61M 5/14* (2006.01)
*A61M 25/06* (2006.01)

(52) U.S. Cl.
CPC .......... *A61M 25/0026* (2013.01); *A61M 5/14* (2013.01); *A61M 25/0606* (2013.01); *A61M 25/0097* (2013.01)

(58) Field of Classification Search
CPC .............. A61M 25/06; A61M 25/0023; A61M 2025/0004; A61M 2025/0681; A61M 25/0606; A61M 25/0026; A61M 2025/0175; A61M 2025/0177
See application file for complete search history.

(56) References Cited

U.S. PATENT DOCUMENTS

| | | | |
|---|---|---|---|
| 3,185,152 A | 5/1965 | Ring | |
| 3,262,448 A | 7/1966 | Ring et al. | |
| 4,068,659 A | 1/1978 | Moorehead | |
| 4,079,738 A | 3/1978 | Dunn et al. | |

(Continued)

FOREIGN PATENT DOCUMENTS

| EP | 2272432 | 1/2011 |
|---|---|---|
| EP | 2569046 | 3/2013 |

(Continued)

OTHER PUBLICATIONS

Velano Vascular, "Introducing PIVO", http://velanovascular.com/solutions/, 2017.

*Primary Examiner* — Bhisma Mehta
*Assistant Examiner* — John J Crawford
(74) *Attorney, Agent, or Firm* — Kirton McConkie; Craig Metcalf; Kevin Stinger

(57) ABSTRACT

A delivery device for delivering an catheter into an intravenous catheter assembly may include a housing having a distal end, a proximal end, and a slot. The delivery device may include a catheter having a proximal end and a distal end. The delivery device may include a catheter hub disposed within the housing. The catheter may be secured to the catheter hub. A portion of the catheter hub may extend through the slot and may be moveable along the slot to advance the catheter in a distal direction. The distal end of the catheter may be disposed distal to the distal end of the housing when the catheter is advanced.

5 Claims, 9 Drawing Sheets

(56) References Cited

U.S. PATENT DOCUMENTS

| | | | | |
|---|---|---|---|---|
| 4,417,886 A | * | 11/1983 | Frankhouser | A61M 25/0606 |
| | | | | 600/435 |
| 4,795,434 A | | 1/1989 | Kujawski | |
| 6,524,299 B1 | * | 2/2003 | Tran | A61M 25/0009 |
| | | | | 604/523 |
| 2007/0088279 A1 | | 4/2007 | Shue et al. | |
| 2007/0088295 A1 | | 4/2007 | Bankiewicz | |
| 2010/0210934 A1 | * | 8/2010 | Belson | A61B 17/3415 |
| | | | | 600/371 |
| 2012/0016307 A1 | | 1/2012 | Burkholz et al. | |
| 2012/0197200 A1 | | 8/2012 | Belson | |
| 2014/0343456 A1 | | 11/2014 | Cabot | |
| 2014/0364766 A1 | * | 12/2014 | Devgon | A61B 5/150221 |
| | | | | 600/581 |
| 2017/0120001 A1 | | 5/2017 | Hyer et al. | |

FOREIGN PATENT DOCUMENTS

| | | |
|---|---|---|
| GB | 1066751 | 4/1967 |
| WO | 98/39054 | 9/1998 |

\* cited by examiner

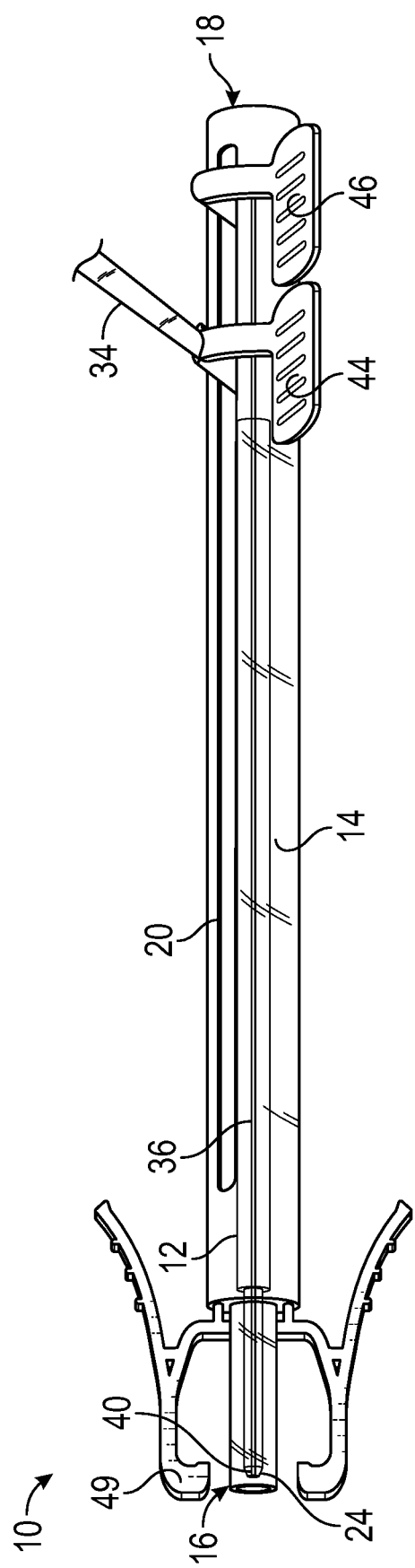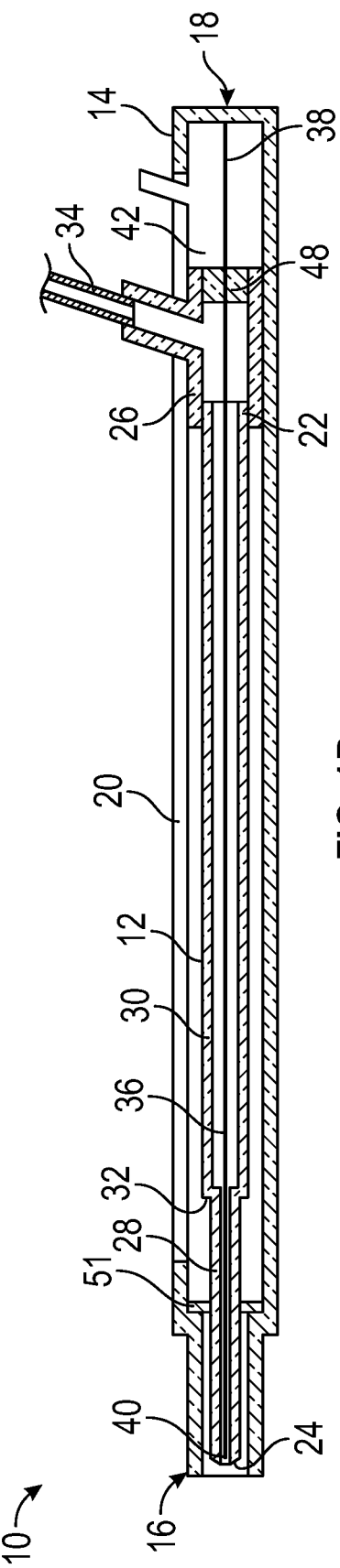
FIG. 1A
FIG. 1B

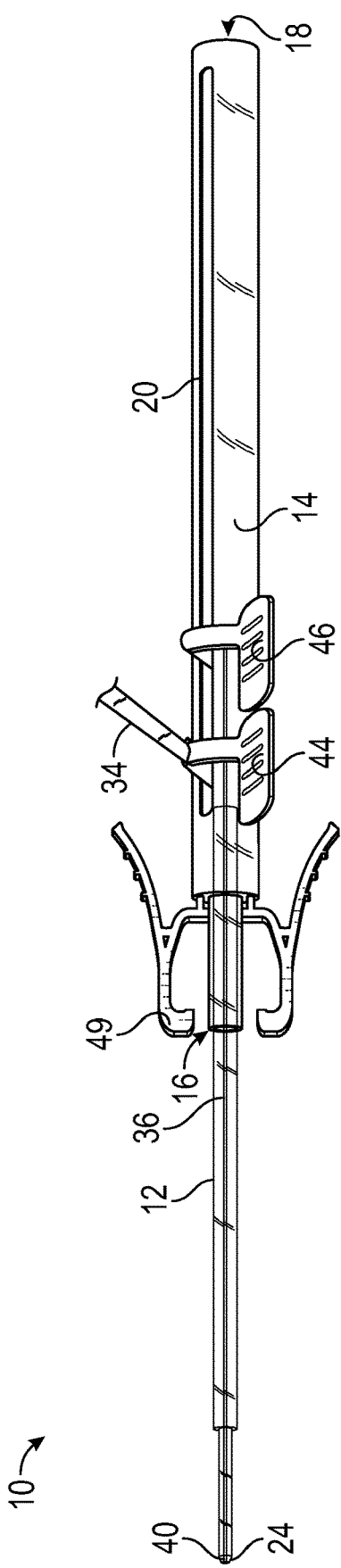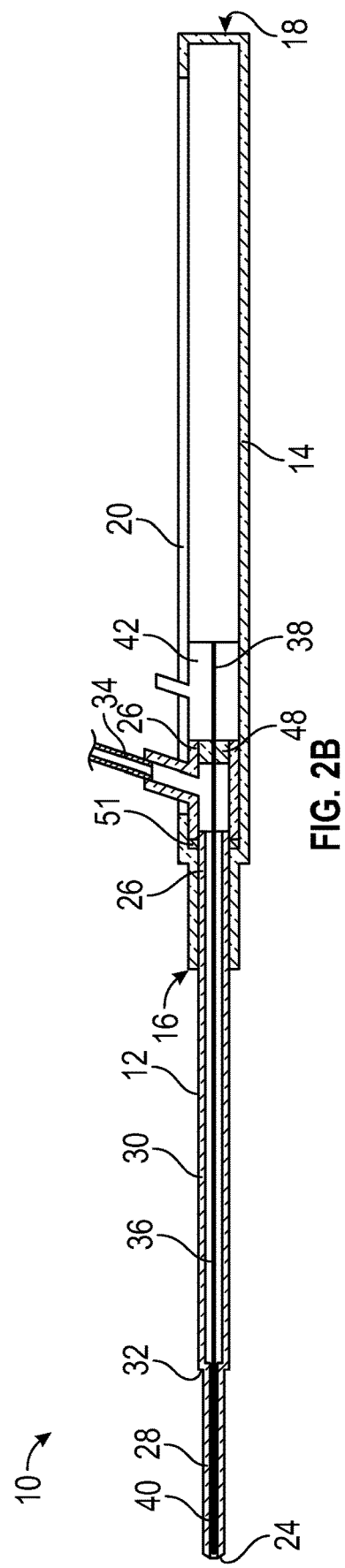

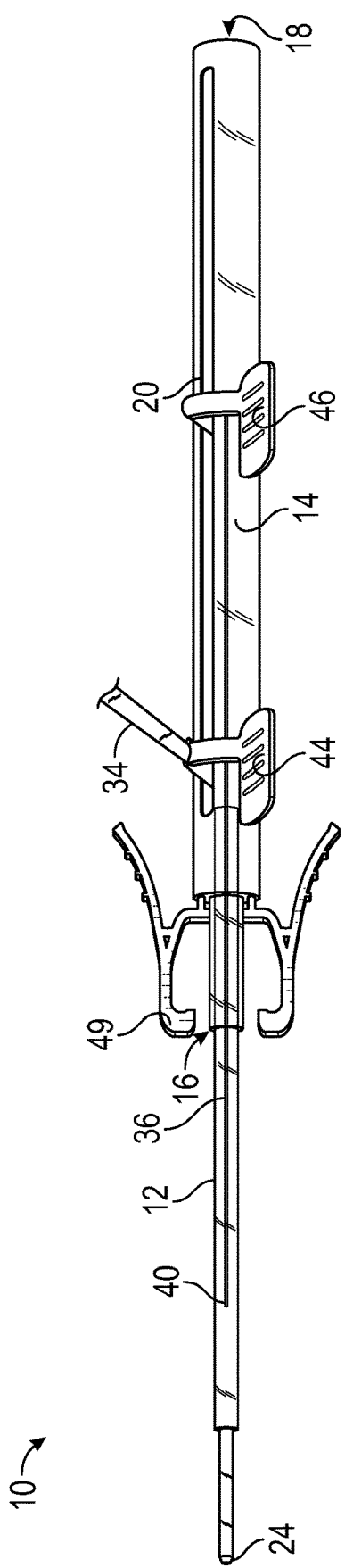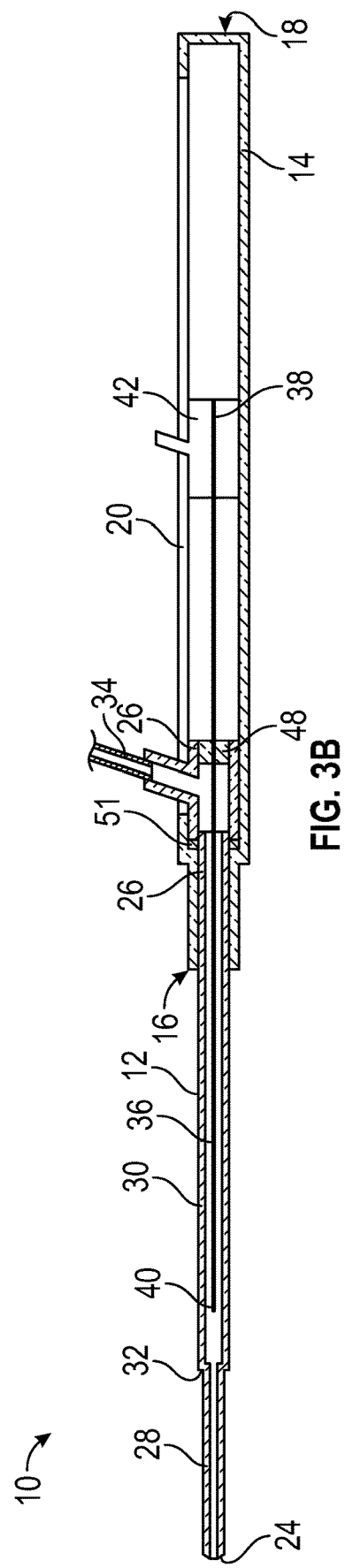

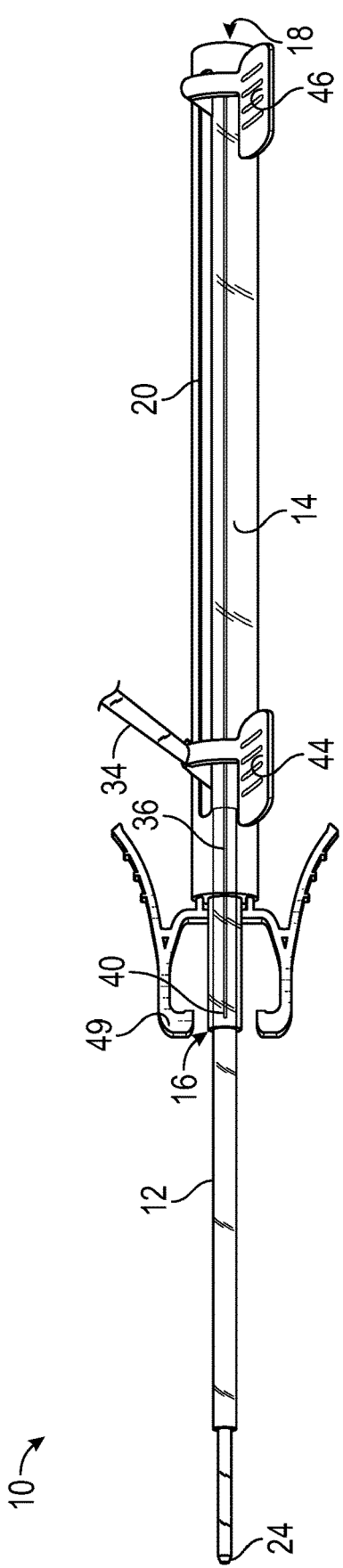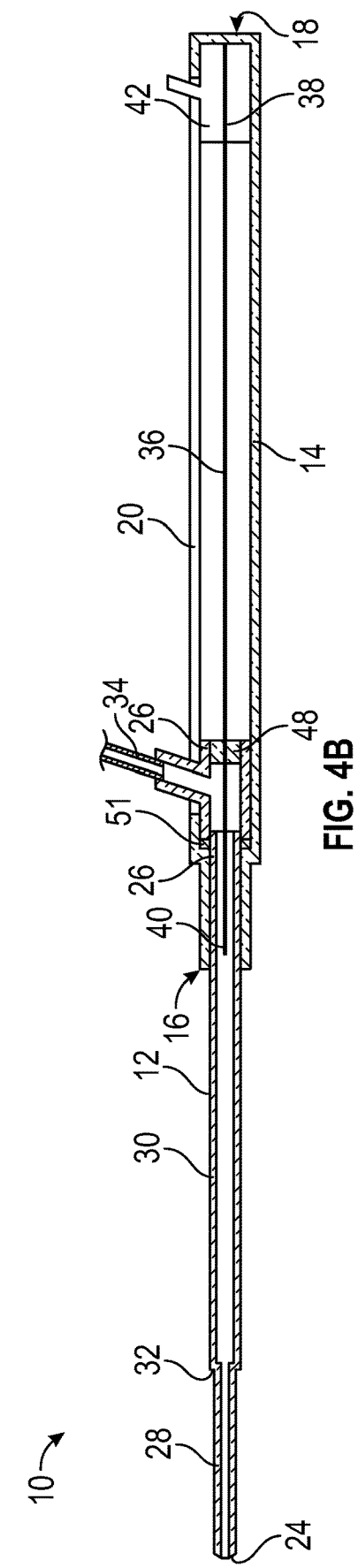
FIG. 4A
FIG. 4B

MULTI-DIAMETER CATHETER AND RELATED DEVICES AND METHODS

RELATED APPLICATIONS

This application claims the benefit of U.S. Provisional Patent Application No. 62/660,646 filed Apr. 20, 2018, entitled MULTI-DIAMETER CATHETER AND RELATED DEVICES AND METHODS, which is incorporated herein in its entirety.

BACKGROUND

Infusion therapy, a common healthcare procedure, may be facilitated by a vascular access device. Hospitalized, home care, and other patients receive fluids, pharmaceuticals, and blood products via a vascular access device inserted into the vascular system. Blood withdrawal is another common healthcare procedure that may be facilitated by a vascular access device.

A vascular access device may access a peripheral or central vasculature of a patient. A vascular access device may be indwelling for short term (days), moderate term (weeks), or long term (months to years). A vascular access device may be used for continuous infusion therapy or for intermittent therapy.

A common type vascular access device is an over-the-needle peripheral intravenous catheter (PIVC). As its name implies, the "over-the-needle" PIVC may be mounted over an introducer needle having a sharp distal tip. The sharp distal tip may be used to pierce skin and the vasculature of the patient. Insertion of the PIVC into the vasculature may follow the piercing of the vasculature by the needle. The needle and the PIVC are generally inserted at a shallow angle through the skin into the vasculature of the patient with a bevel of the needle facing away from the skin of the patient. Once placement of the needle within the vasculature has been confirmed, the clinician may temporarily occlude flow in the vasculature and withdraw the needle, leaving the PIVC in place for future fluid infusion and/or blood withdrawal.

Currently, there may be several limitations to the use of a PIVC for fluid infusion or blood draw. The PIVC or vein may narrow, collapse, or clog with time, leading to failure of the PIVC. Also, blood extracted from PIVCs may often need to be discarded due to concerns regarding sample quality, which may result in an unusable sample and a need to repeat blood collection. Further, use of a PIVC to draw blood can be slow and somewhat inefficient, particularly when the patient has difficult intravenous access or veins that are not readily accessed by the clinician.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access systems, devices, and methods. More particularly, in some embodiments, the present disclosure relates to systems, devices, and methods for placing a first catheter within a second catheter and/or a vein of a patient. In some embodiments, the second catheter may include an indwelling PIVC. In some embodiments, the first catheter may allow a user to draw a blood sample or infuse fluid through the second catheter when the second catheter is no longer functional or less effective due to, for example, debris build up on a distal end of the second catheter or collapse of the second catheter. Thus, in some embodiments, the first catheter may reduce a number of needle sticks that a patient experiences as the second catheter may be replaced less frequently.

In some embodiments, a delivery device for delivering the first catheter into an intravenous catheter assembly and/or the vein may include a housing, which may include a distal end, a proximal end, and a slot. In some embodiments, the delivery device may include the first catheter, which may include a proximal end and a distal end. In some embodiments, the delivery device may include a catheter hub, which may be disposed within the housing. In some embodiments, the first catheter may be secured to the catheter hub. In some embodiments, a portion of the catheter hub may extend through the slot and may be moveable along the slot to advance the catheter in a distal direction and/or retract the catheter in a proximal direction. In some embodiments, the distal end of the first catheter may be disposed distal to the distal end of the housing when the first catheter is fully and/or partially advanced.

In some embodiments, the first catheter may include a first portion and a second portion. In some embodiments, the first portion may include a first inner diameter along an entire length of the first portion and a first outer diameter along the entire length of the first portion. In some embodiments, the second portion may be disposed proximal to the first portion. In some embodiments, the second portion may include a second inner diameter and a second outer diameter along an entire length of the second portion. In some embodiments, the second inner diameter may be greater than the first inner diameter. In some embodiments, the second outer diameter may be greater than the first outer diameter. In some embodiments, the first portion may include the distal end of the catheter.

In some embodiments, the first catheter may include a third portion, which may be disposed proximal to the second portion. In some embodiments, the third portion may include a third inner diameter along an entire length of the third portion and a third outer diameter along an entire length of the third portion. In some embodiments, the third inner diameter may be greater than the second inner diameter. In some embodiments, the third outer diameter may be greater than the second outer diameter. In some embodiments, the third portion may include the proximal end of the first catheter.

In some embodiments, the first catheter may include a transition portion disposed between the first portion and the second portion and/or another transition portion disposed between the second portion and the third portion. In some embodiments, at least a portion of an outer surface of the transition portion may be tapered and/or stepped. In some embodiments, at least a portion of an inner surface of the transition portion may be tapered and/or stepped. In some embodiments, at least a portion of an outer surface of the other transition portion may be tapered and/or stepped. In some embodiments, at least a portion of an inner surface of the other transition portion may be tapered and/or stepped.

In some embodiments, the portion of the catheter hub that extends through the slot may be coupled to a blood collection device. In some embodiments, the first catheter may extend through or near the proximal end of the housing, and the proximal end of the first catheter may be coupled to the blood collection device.

In some embodiments, the delivery device may include a guidewire, which may include a proximal end and a distal end. In some embodiments, the guidewire may be disposed within the first catheter. In some embodiments, a guidewire hub may be disposed within the housing proximal to the catheter hub. In some embodiments, the guidewire may be secured to the guidewire hub. In some embodiments, a portion of the guidewire hub may extend through the slot and may be moveable along the slot to advance the guidewire in the distal direction and/or retract the guidewire in a proximal direction. In some embodiments, the distal end of the guidewire may be disposed distal to the distal end of the housing when the guidewire is fully and/or partially advanced.

In some embodiments, the guidewire may be partially or fully retracted when the first catheter is advanced. In some embodiments, when the first catheter is fully advanced in the distal direction and the guidewire is fully advanced in the distal direction, the distal end of the guidewire may be approximately aligned with the distal end of the first catheter.

In some embodiments, the catheter hub may include an advancement tab, which may be coupled to the portion of the catheter hub that extends through the slot. In some embodiments, the guidewire hub may include another advancement tab, which may be coupled to the portion of the guidewire hub that extends through the slot.

In some embodiments, an intravenous catheter system may include the catheter assembly, which may include a catheter adapter and the second catheter. In some embodiments, the catheter adapter may include a distal end, a proximal end, and a lumen extending between the distal end and the proximal end. In some embodiments, the catheter adapter may include a side port. In some embodiments, the second catheter may be secured to the catheter adapter and may extend distally from the catheter adapter.

In some embodiments, an extension set may be coupled to the catheter adapter. In some embodiments, the extension set may include an extension tube, which may include a distal end and a proximal end. In some embodiments, the extension tube may extend from the side port. In some embodiments, the extension tube may extend from the proximal end of the catheter adapter, which may be axially aligned with the distal end of the catheter adapter. In some embodiments, the extension set may include a connector, which may be coupled to the proximal end of the extension tube.

In some embodiments, the catheter system may include the delivery device. In some embodiments, the transition portion may be disposed within the lumen of the catheter adapter when the first catheter is fully and/or partially advanced. In some embodiments, the other transition portion may be disposed within a lumen of the extension tube when the first catheter is fully and/or partially advanced. In some embodiments, the catheter system may include the guidewire and/or the guidewire hub. In some embodiments, the distal end of the guidewire may be disposed distal to the distal end of the second catheter when the guidewire is fully and/or partially advanced.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 1A is an upper perspective view of an example delivery device, illustrating an example catheter and example guidewire each in a fully retracted position, according to some embodiments;

FIG. 1B is a cross-sectional view of the delivery device of FIG. 1A, illustrating the catheter and the guidewire each in the fully retracted position, according to some embodiments;

FIG. 2A is an upper perspective view of the delivery device of FIG. 1A, illustrating the catheter and the guidewire each in a fully advanced position, according to some embodiments;

FIG. 2B is a cross-sectional view of the delivery device of FIG. 1A, illustrating the catheter and the guidewire each in the fully advanced position, according to some embodiments;

FIG. 3A is an upper perspective view of the delivery device of FIG. 1A, illustrating the catheter in the fully advanced position and the guidewire in a partially retracted position, according to some embodiments;

FIG. 3B is a cross-sectional view of the delivery device of FIG. 1A, illustrating the catheter in the advanced position and the guidewire in the partially retracted position, according to some embodiments;

FIG. 4A is an upper perspective view of the delivery device of FIG. 1A, illustrating the catheter in the fully advanced position and the guidewire in the fully retracted position, according to some embodiments;

FIG. 4B is a cross-sectional view of the delivery device of FIG. 1A, illustrating the catheter in the fully advanced position and the guidewire in the fully retracted position, according to some embodiments;

DESCRIPTION OF EMBODIMENTS

Figure 5A:
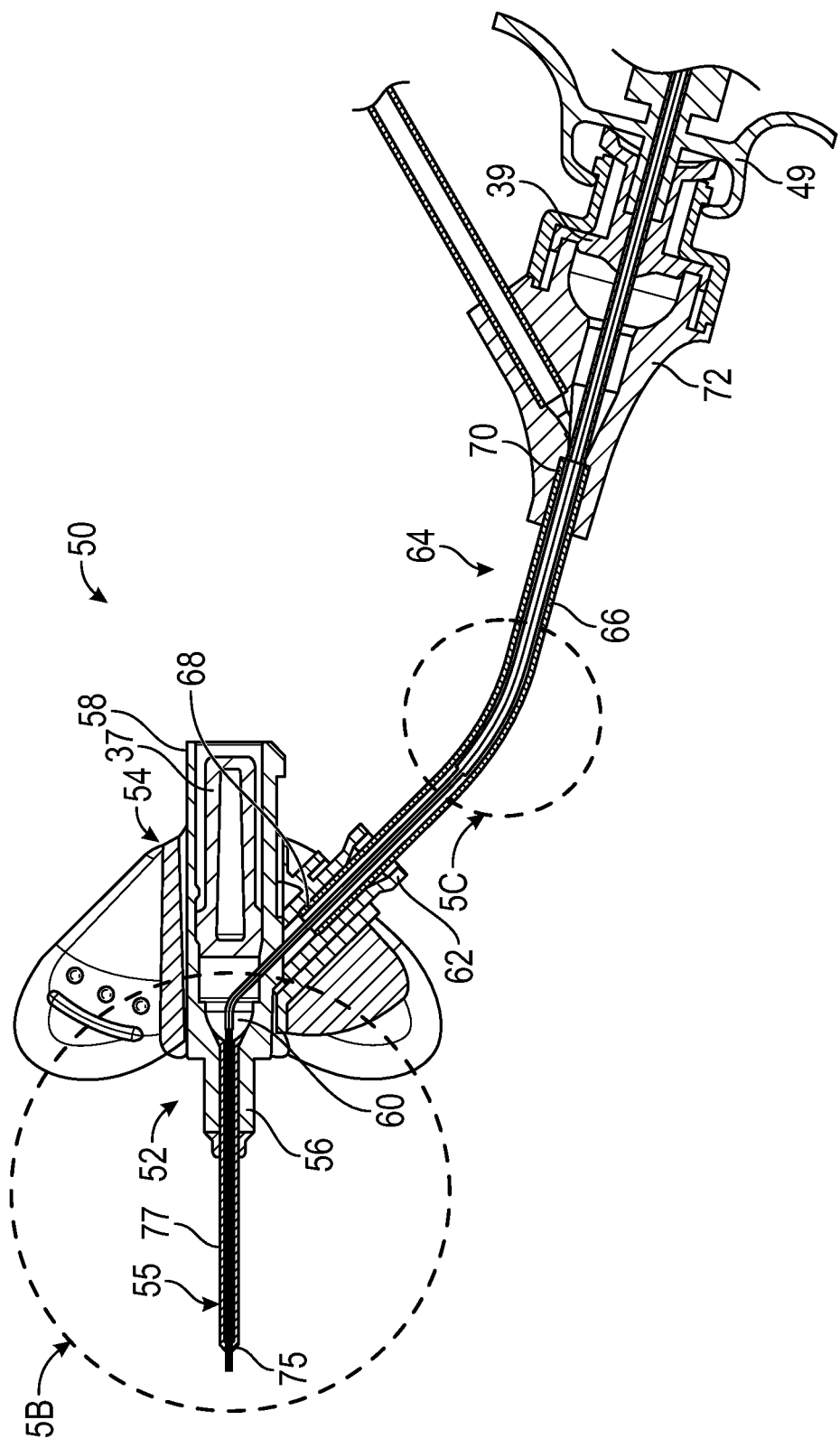
FIG. 5A is a cross-sectional view of an example catheter system that includes the delivery device of FIG. 1A, illustrating the catheter and the guidewire each in the fully advanced position, according to some embodiments.

The present disclosure relates generally to vascular access systems, devices, and methods. More particularly, in some embodiments, the present disclosure relates to systems, devices, and methods for placing a first catheter within a second catheter and/or a vein of a patient. In some embodiments, the second catheter may include an indwelling PIVC. In some embodiments, the second catheter may be a small gauge catheter, such as, for example, 26, 24, or 22 gauge, or a large gauge catheter, such as, for example, 20 gauge or above.

Referring now to FIG. 1A-1B, in some embodiments, a delivery device 10 for delivering a catheter 12 into an intravenous catheter assembly and/or the vein may include a housing 14, which may include a distal end 16, a proximal end 18, and a slot 20. In some embodiments, the delivery device 10 may include the catheter 12, which may include a proximal end 22 and a distal end 24.

In some embodiments, the delivery device 10 may include a catheter hub 26, which may be disposed within the housing 14. In some embodiments, the catheter 12 may be secured to the catheter hub 26. In some embodiments, the proximal end 22 of the catheter 12 may be secured to the catheter hub 26, as illustrated, for example, in FIG. 1B. In some embodiments, a portion of the catheter hub 26 may extend through the slot 20 and may be moveable along the slot 20 to advance the catheter 12 in a distal direction and/or retract the catheter 12 in a proximal direction. In some embodiments, the distal end 24 of the catheter 12 may be disposed distal to the distal end 16 of the housing 14 when the catheter 12 is fully and/or partially advanced.

In some embodiments, the catheter 12 may include a first portion 28 and a second portion 30. In some embodiments, the first portion 28 may include a first inner diameter along an entire length of the first portion 28 and a first outer diameter along the entire length of the first portion 28. In some embodiments, the second portion 30 may be disposed proximal to the first portion 28. In some embodiments, the second portion 30 may include a second inner diameter and a second outer diameter along an entire length of the second portion 30. In some embodiments, the second inner diameter may be greater than the first inner diameter. In some embodiments, the second outer diameter may be greater than the first outer diameter. In some embodiments, the first portion 28 may include the distal end 24 of the catheter 12. In some embodiments, the distal end 24 of the catheter 12 may include a tapered tip, which may be disposed proximate and distal to the first portion 28. In some embodiments, the second portion 30 may include the proximal end 22 of the catheter 12.

In some embodiments, the catheter 12 may include a third portion, which may be disposed proximal to the second portion 30. In some embodiments, the third portion may include a third inner diameter along an entire length of the third portion and a third outer diameter along an entire length of the third portion. In some embodiments, the third inner diameter may be greater than the second inner diameter. In some embodiments, the third outer diameter may be greater than the second outer diameter. In some embodiments, the third portion may include the proximal end of the catheter 12. Example third portions are illustrated in FIGS. 5A and 5C-5D and FIG. 8.

In some embodiments, the catheter 12 may include a transition portion 32 disposed between the first portion 28 and the second portion 30 and/or another transition portion (illustrated, for example, in FIG. 5C or FIG. 8) disposed between the second portion 30 and the third portion. In some embodiments, at least a portion of an outer surface of the transition portion 32 may be tapered and/or stepped. In some embodiments, the outer surface of the transition portion 32 may include various shapes or combination of shapes. For example, a first portion of the outer surface of the transition portion 32 may be gradually tapered and a second portion of the outer surface of the transition portion 32 may be stepped. In some embodiments, at least a portion of an inner surface of the transition portion 32 may be tapered and/or stepped. In some embodiments, the inner surface of the transition portion 32 may include various shapes or combination of shapes. For example, a first portion of the inner surface of the transition portion 32 may be gradually tapered and a second portion of the inner surface of the transition portion 32 may be stepped. In some embodiments, the inner surface of the transition portion 32 and/or the outer surface of the transition portion 32 may be linearly tapered along all or a portion of the length of the transition portion 32.

In some embodiments, at least a portion of an outer surface of the other transition portion may be tapered and/or stepped. In some embodiments, the outer surface of the other transition portion may include various shapes or combination of shapes. For example, a first portion of the outer surface of the transition portion may be gradually tapered and a second portion of the outer surface of the other transition portion may be stepped. In some embodiments, at least a portion of an inner surface of the other transition portion may be tapered and/or stepped. In some embodiments, the inner surface of the other transition portion may include various shapes or combination of shapes. For example, a first portion of the inner surface of the other transition portion may be gradually tapered and a second portion of the inner surface of the other transition portion may be stepped. In some embodiments, the inner surface of the transition portion and/or the outer surface of the other transition portion may be linearly tapered along all or a portion of the length of the other transition portion.

In some embodiments, the portion of the catheter hub 26 that extends through the slot 20 may be coupled to a blood collection device. In some embodiments, the portion of the catheter hub 26 that extends through the slot 20 may be directly coupled to the blood collection device. In some embodiments, the portion of the catheter hub 26 that extends through the slot 20 may be coupled to the blood collection device via extension tubing 34, which may include a connector on a proximal end of the extension tubing for connecting the blood sampling device to the extension tubing 34. In some embodiments, the connector may be disposed on the portion of the catheter hub 26 that extends through the slot 20. In some embodiments, a fluid pathway of the catheter system 50 may include the catheter 12, the catheter hub 26, and the extension tubing 34.

In some embodiments, the delivery device 10 may include a guidewire 36, which may include a proximal end 38 and a distal end 40. In some instances, the guidewire 36 may be used to facilitate placement of the catheter 12 within the vein of the patient, which may result in less vein-related trauma and may support the catheter 12 during advancement to prevent collapse or buckling of the catheter 12 as it advances through a second catheter (such as, for example, the catheter 55 illustrated in FIGS. 5-6) Upon successful placement of the catheter 12 within the vein, the guidewire may be retracted.

In some embodiments, the guidewire 36 may be disposed within the catheter 12. In some embodiments, an outer diameter of the guidewire 36 may be less than an inner diameter of the catheter 12 such that fluid may flow into through the catheter 12. In some embodiments, the fluid may flow between an outer surface of the guidewire 36 and an inner surface of the catheter 12. In some embodiments, a guidewire hub 42 may be disposed within the housing 14 proximal to the catheter hub 26.

In some embodiments, the guidewire 36 may be secured to the guidewire hub 42. In some embodiments, the proximal end 38 of the guidewire 36 may be secured to the guidewire hub 42, as illustrated, for example, in FIG. 1B. In some embodiments, a portion of the guidewire hub 42 may extend through the slot 20 and may be moveable along the slot 20 to advance the guidewire in the distal direction and/or retract the guidewire in the proximal direction.

FIGS. 1A-1B illustrate both the guidewire 36 and the catheter 12 in a fully retracted position, prior to advancing the guidewire 36 or the catheter 12 in the distal direction or after returning the catheter 12 and/or the guidewire 36 from an advanced position, according to some embodiments. In some embodiments, when the guidewire hub 42 is fully retracted proximally to retract the guidewire 36, the guidewire hub 42 may contact a proximal end of the slot 20 and/or the proximal end 18 of the housing 14, which may act as a stop.

In some embodiments, the catheter hub 26 may include an advancement tab 44, which may be coupled to the portion of the catheter hub 26 that extends through the slot 20. In some embodiments, the guidewire hub 42 may include another advancement tab 46, which may be coupled to the portion of the guidewire hub 42 that extends through the slot 20. In some embodiments, the advancement tab 44 and the advancement tab 46 may be disposed proximate or near each other so as to be simultaneously moved or pinched by a hand of a user, according to some embodiments. In some embodiments, the advancement tab 44 and the advancement tab 46 may include platforms that may be aligned or positioned in a same plane. In some embodiments, the advancement tabs 44 and/or the advancement tab 46 may include various shapes, sizes, and configurations.

In some embodiments, the catheter hub 26 may include a septum 48, which may prevent fluid, such as blood, from moving proximal to the catheter hub 26. In some embodiments, the guidewire 36 may extend through the septum 48.

In some embodiments, the delivery device 10 may include a connector 49, which may be configured to couple the delivery device 10 to a catheter system. In some embodiments, the connector 49 may include a luer adapter, such as a slip or thread male or female luer adapter, or another suitable connector.

In some embodiments, the delivery device 10 may include a blood control septum 51, which may be disposed within a lumen of the delivery device 10. In some embodiments, the septum 51 may be disposed proximate or towards the distal end 16 of the delivery device 10. In some embodiments, the catheter 12 may penetrate the septum 51 in response to the catheter 12 being advanced. In some embodiments, the septum 51 may prevent blood from travelling between the catheter 12 and an inner surface of the delivery device 10 such that blood may not enter at least a portion of the delivery device 10.

Referring now to FIGS. 2A-2B, the catheter hub 26 and the guidewire hub 42 may be fully advanced, according to some embodiments. In some embodiments, when the catheter hub 26 is fully advanced in the distal direction to fully advance the catheter 12, the catheter hub 26 may contact a distal end of the slot 20 and/or an inner surface of the housing 14, which may act as a stop. In some embodiments, the guidewire hub 42 may contact a proximal end of the catheter hub 26 in response to the guidewire hub 42 being fully advanced.

In some embodiments, the distal end 40 of the guidewire 36 may be disposed distal to the distal end 16 of the housing 14 when the guidewire 36 is fully and/or partially advanced. In some embodiments, when the catheter 12 is fully advanced in the distal direction and the guidewire is fully advanced in the distal direction, the distal end 40 of the guidewire 36 may be approximately aligned with the distal end 24 of the catheter 12. In some embodiments, movement of the guidewire hub 42 in the distal direction may also move the catheter hub 26 in the distal direction, advancing both the guidewire 36 and the catheter 12. In some embodiments, movement of the catheter hub 26 in the proximal direction may also move the guidewire hub 42 in the proximal direction, retracting the guidewire 36 and the catheter 12. In some embodiments, the catheter hub 26 and the guidewire hub 42 may be configured to move independently of each other.

Referring now to FIGS. 3A-3B, in some embodiments, the guidewire 36 may be partially retracted when the catheter 12 is advanced. In some embodiments, the guidewire 36 may be partially retracted such that the distal end 40 of the guidewire is disposed in the first portion 28 or the second portion 30. In some embodiments, the first inner diameter of the first portion 28 and/or the second inner diameter of the second portion 30 may allow improved blood flow rates during blood collection. In further detail, in some embodiments, the outer diameter of the guidewire 36 may be less than the first inner diameter of the first portion 28 and/or the second inner diameter of the second portion 30, which may allow blood to flow around the guidewire 36 during blood collection. Referring now to FIGS. 4A-4B, in some embodiments, the guidewire 36 may be fully retracted when the catheter 12 is advanced. In some embodiments, blood flow rates through the catheter 12 may be even greater when the guidewire 36 is fully retracted compared to when the guidewire 36 is partially retracted.

Figure 5B:
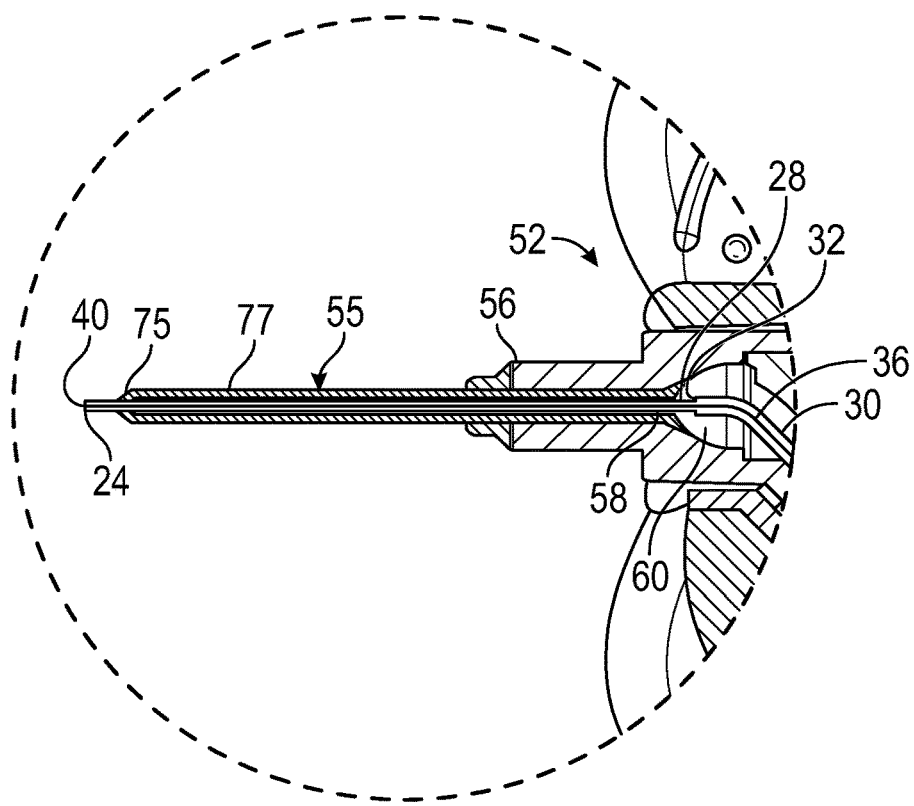
FIG. 5B is an enlarged cross-sectional view of a portion of the catheter system of FIG. 5A, according to some embodiments.
Figure 5C:
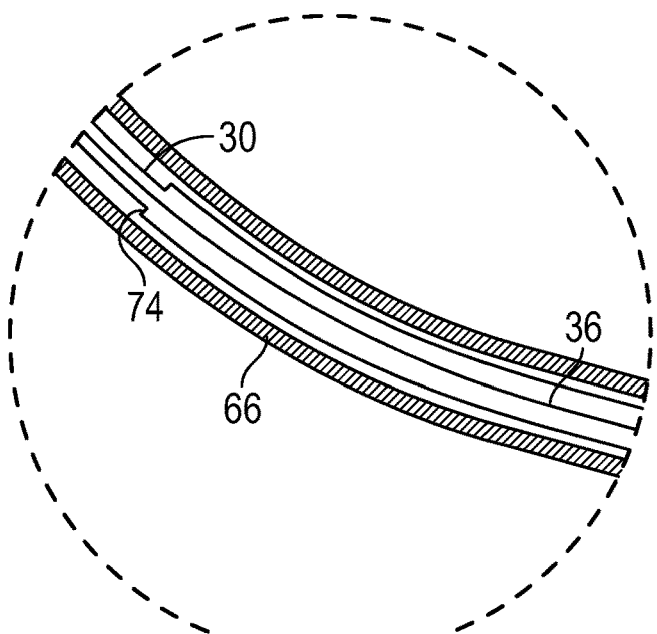
FIG. 5C is an enlarged cross-sectional view of another portion of the catheter system of FIG. 5A, according to some embodiments.

Referring now to FIGS. 5A-5C, in some embodiments, an intravenous catheter system 50 may include a catheter assembly 52, which may include a catheter adapter 54 and a catheter 55, which may be indwelling. In some embodiments, the catheter 55 may include a PIV catheter. In some embodiments, the catheter adapter 54 may include a distal end 56, a proximal end 58, and a lumen 60 extending between the distal end 56 and the proximal end 58. In some embodiments, the distal end 56 and the proximal end 58 of the catheter adapter 54 may be axially aligned. In some embodiments, the catheter adapter 54 may include a side port 62. In some embodiments, the catheter 55 may be secured to the catheter adapter 54 and may extend distally from the catheter adapter 54.

In some embodiments, an extension set 64 may be coupled to the catheter adapter 54. In some embodiments, the extension set 64 may include extension tubing 66, which may include a distal end 68 and a proximal end 70. In some embodiments, the extension tubing 66 may extend from the side port 62. In some embodiments, the extension set 64 may include a connector 72, which may be coupled to the proximal end 70 of the extension tubing 66. In some embodiments, the connector 72 may include a luer adapter, such as a male or female luer adapter, or another suitable connector. In some embodiments, the distal end 68 of the extension tubing 66 may be fixed to or integrally formed with the side port 62.

In some embodiments, the catheter system 50 may include the delivery device 10. In some embodiments, the catheter system 50 may include the guidewire 36 and/or the guidewire hub 42. In some embodiments, the distal end 40 of the guidewire 36 and/or the distal end 24 of the catheter 12 may be disposed distal to the distal end of the catheter 55 when the guidewire 36 is fully and/or partially advanced.

In some embodiments, the catheter 12 may provide structural support to the catheter 55. In some embodiments, the catheter 12 may allow the user to draw a blood sample or infuse fluid through the catheter 55 when the catheter 55 is no longer functional or safe due to, for example, debris build up on the tip 75 of the catheter 55 and/or collapse of the catheter 55. Thus, in some embodiments, the catheter 12 may reduce a number of needle sticks that the patient experiences as the catheter 55 may be replaced less frequently.

In some embodiments, delivery of the catheter 12 into the catheter system 50 and/or the vasculature of the patient may reduce blood hemolysis and a risk of kinking of the catheter 55. In some embodiments, the delivery device 10 may allow use of the guidewire 36, which may improve placement of the catheter 12 within the vasculature. In some embodiments, the connector 72 may be disposed remotely from the patient, which may reduce a risk of disturbing an insertion site of the catheter 55.

In some embodiments, the transition portion 32 may be disposed within the lumen 60 of the catheter adapter 54 when the catheter 12 is fully and/or partially advanced. In some embodiments, the other transition portion 74 may be disposed within a lumen of the extension tubing 66 when the catheter 12 is fully and/or partially advanced. In some embodiments, when the catheter 12 is fully and/or partially advanced, the transition portion 32 may be disposed within the catheter 55 proximal and/or proximate the tip 75 of the catheter 55, which may be narrowed compared to a body 77 of the catheter 55.

In some embodiments, the transition portion 32 and/or the other transition may decrease a blood collection time because the catheter 12 may transition to a larger inner diameter in wider portions of the catheter system 50, allowing blood to flow through the catheter 12 more rapidly. In some embodiments, the first outer diameter of the first portion 28 may be approximately equal to or slightly less than an inner diameter of a tip 75 of the catheter 55. In some embodiments, the second outer diameter of the second portion 30 may be approximately equal to or slightly less than an inner diameter of the body 77 of the catheter 55. In some embodiments, the third outer diameter of the third portion may be approximately equal to or slightly less than an inner diameter of the extension tubing 66.

In some embodiments, the catheter 12 may include any number of transition portions, which may be similar to the transition portion 32 and the transition portion 74. In some embodiments, each of the particular transition portions of the catheter 12 may be disposed between a section of the catheter 12 having a uniform inner diameter and a uniform outer diameter. In some embodiments, the catheter 12 may include only one transition portion, only two transition portions, or only three transition portions. In some embodiments, the catheter 12 may include more than three transition portions. In some embodiments, a number of transition portions of the catheter 12 may correspond to a number of areas of widening of a pathway of the catheter 12 through the catheter system 50. In some embodiments, when the catheter 12 is fully and/or partially advanced, the transition portion 32 may be disposed within the catheter 55 proximal and/or proximate the tip 74 of the catheter 55, which may be tapered. In some embodiments, when the catheter 12 is fully and/or partially advanced, the transition portion 74 may be disposed within the lumen 60 of the catheter adapter 54. In some embodiments, another transition portion proximal to the transition portion 32 and the transition portion 74 may be disposed within a lumen of the extension tubing 66 when the catheter 12 is fully and/or partially advanced.

In some embodiments, the transition portions may include various shapes or combination of shapes. In some embodiments, the inner surface and/or outer surface of the transition portions may be gradual. Additionally or alternatively, in some embodiments, the inner surface and/or outer surface of the transition portions may be abrupt or stepped.

In some embodiments, the catheter 12 may include tubing. In some embodiments, the tubing may be co-extruded to provide various structural improvements (layers, axial stripes, etc.). In some embodiments, the tubing may be constructed of polyimide, latex, polyurethane, nylon, polyethylene, or another suitable material. In some embodiments, the tubing may be cylindrical. In some embodiments, the catheter 12 may include a tapered tip, a chamfered tip, or a blunt tip. In some embodiments, the transition portions, such as the transition portion 32 and/or the transition portion 74, may be constructed by extrusion of a continuous tube, which may be monolithically formed as a single unit, or by joining multiple tubes of varying inner and outer diameters together. In some embodiments, the multiple tubes may be constructed of a same or different material. In some embodiments, the multiple tubes may bonded, swaged, tipped, welded, or joined via another suitable method.

In some embodiments, the catheter adapter 54 may be integrated, having an integrated extension tube, or non-integrated. In some embodiments, a lubricant, such as, for example, a silicon lubricant, may be disposed between the catheter 12 and a blood control septum 37 of the catheter adapter 54 through which the catheter 12 may travel. In some embodiments, the blood control septum 37 may be disposed within the catheter adapter 54. Additionally or alternatively, a blood control septum 39 may be disposed within the connector 72. In some embodiments, the lubricant may be disposed between the catheter 12 and the septum 39. In some embodiments, the blood control septum 37 and/or the blood control septum 39 may include a slit that maintains a seal when the catheter 12 is advanced and/or retracted. In some embodiments, the delivery device 10 may be compatible with catheter adapters 54 having a blood control septum or not having a blood control septum. In some embodiments, the lubricant may be disposed between the catheter 12 and the septum 48 of the catheter hub 26. In some embodiments, the lubricant may be disposed between the catheter 12 and the septum 51 of the delivery device 10.

Figure 5D:
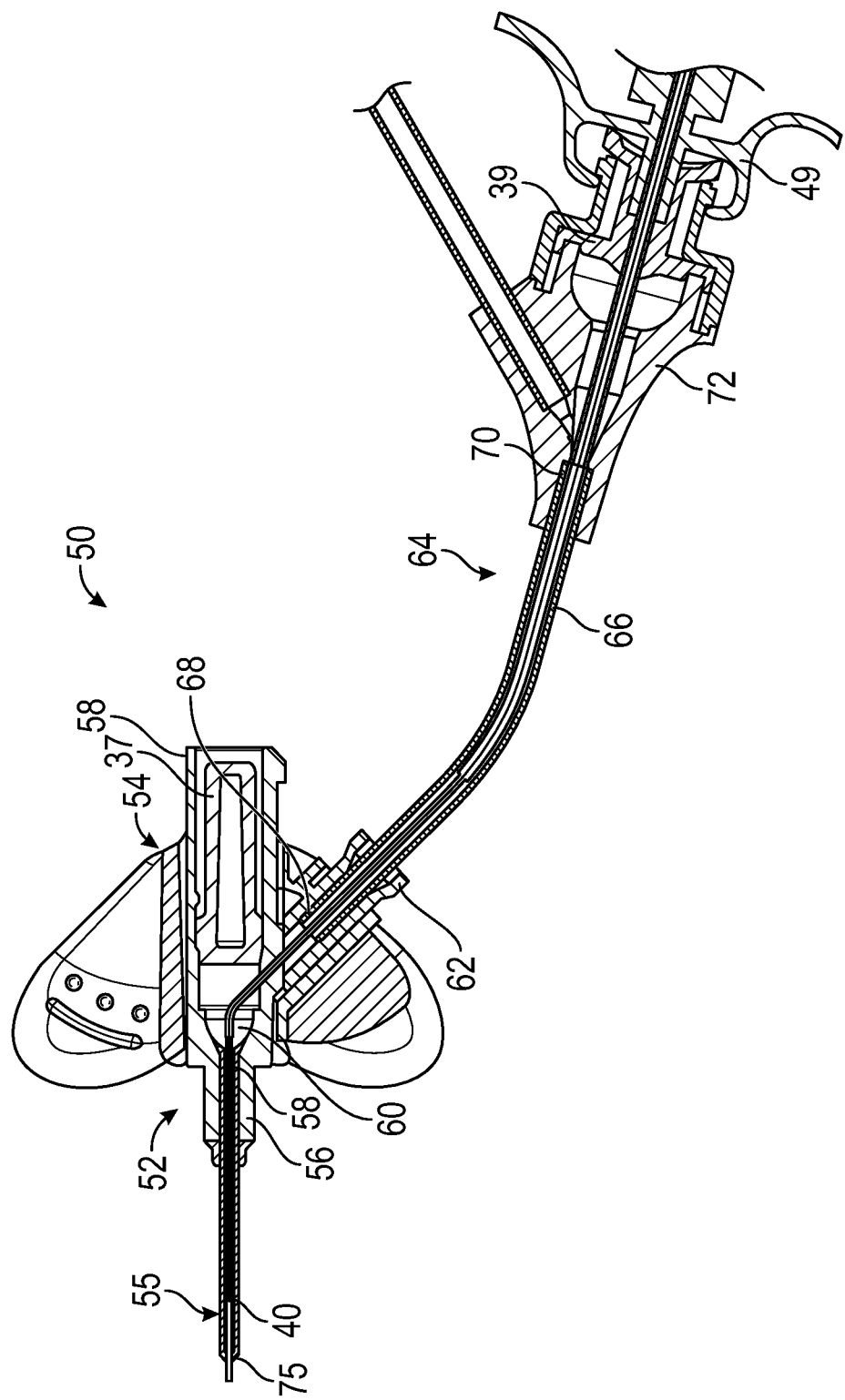
FIG. 5D is a cross-sectional view of the catheter system of FIG. 5A, illustrating the catheter in the fully advanced position and the guidewire in the partially retracted position, according to some embodiments.

Referring now to FIG. 5D, in some embodiments, the distal end 40 of the guidewire 36 may be disposed within a lumen of the catheter 55 when the guidewire 36 is partially and/or fully retracted by proximal movement of the guidewire hub 42. In some embodiments, the distal end 40 of the guidewire 36 may be disposed proximal to the transition portion 32 when the guidewire 36 is partially and/or fully retracted by proximal movement of the guidewire hub 42.

In some embodiments, the guidewire 36 may include an echogenic distal end 40 or a magnetic distal end 40 which may aid in ultra-sound visualization of the distal end 24 of the catheter 12 relative to the vasculature of the patient. In some embodiments, the guidewire 36 may include a blunt distal end 40.

Figure 6A:
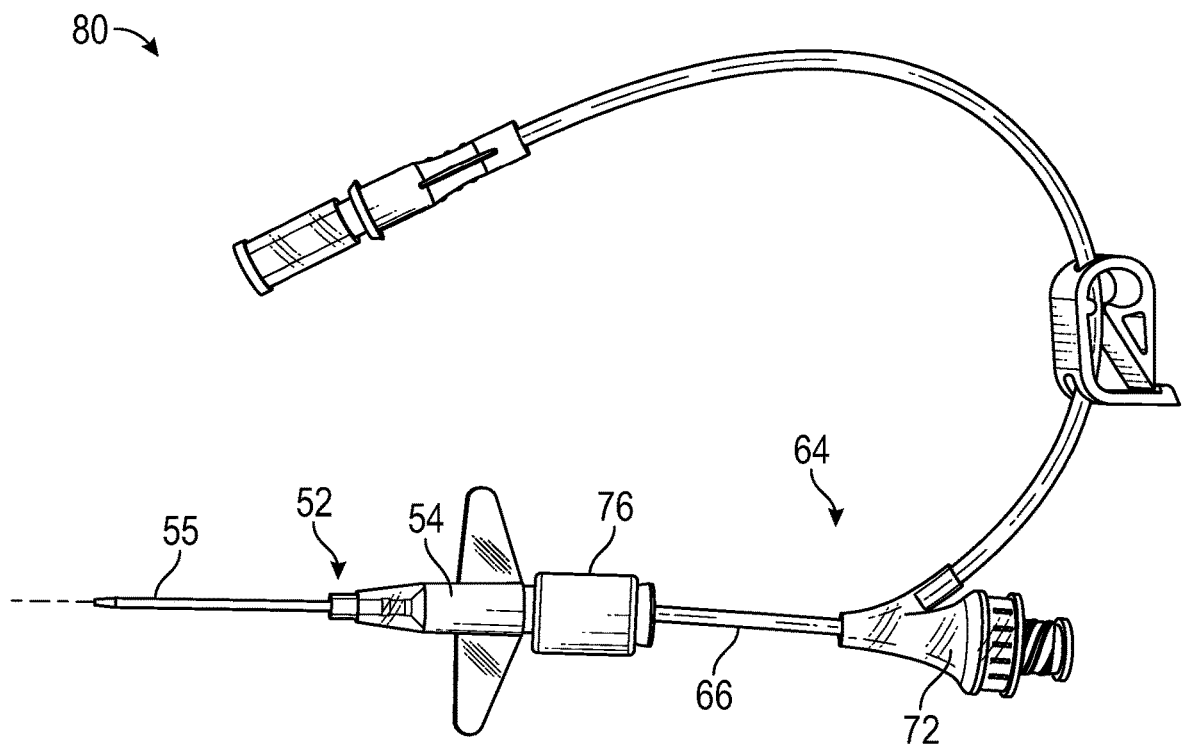
FIG. 6A is an upper perspective view of another example catheter system that may include the delivery device of FIG. 1A, according to some embodiments.
Figure 6B:
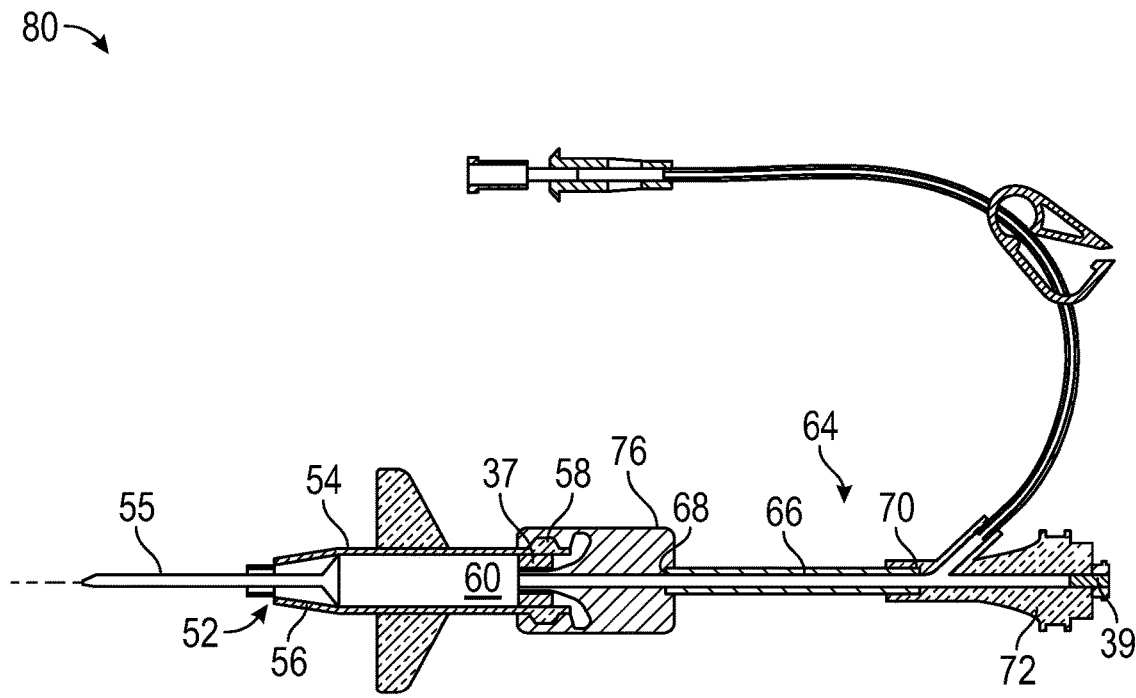
FIG. 6B is a cross-sectional view of the catheter system of FIG. 6A, according to some embodiments.

Referring now to FIGS. 6A-6B, another catheter system 80 is illustrated. In some embodiments, the catheter system 80 may include or correspond to the catheter system 50 of FIG. 5. In further detail, the catheter system 80 may include one or more features of the catheter system 50. In some embodiments, the catheter system 50 may include one or more features of the catheter system 80.

In some embodiments, the extension tubing 66 may extend from the proximal end 58 of the catheter adapter 54, which may be axially aligned with the distal end 56 of the catheter adapter 54. In some embodiments, the connector 72 may be coupled to the proximal end 70 of the extension tubing 66. In some embodiments, the connector 76 may be directly coupled to the connector 72, and the catheter system 80 may not include the extension tubing 66.

In some embodiments, the distal end 68 of the extension tubing 66 may be coupled to the proximal end 58 of the catheter adapter 54. In some embodiments, another connector 76 may be configured to connect the distal end 68 of the extension tubing 66 to the proximal end 58 of the catheter adapter 54. In some embodiments, the connector 76 may selectively or fixedly couple the distal end 68 of the extension tubing 66 to the proximal end 58 of the catheter adapter 54. In some embodiments, the connector 76 may include a luer adapter, such as a male or female luer adapter, or any other suitable connector.

In some embodiments, the connector 76 may be absent. In some embodiments, the extension tubing 66 may be pre-attached to the catheter adapter 54. In these and other embodiments, the distal end 68 of the extension tubing 66 may be fixedly coupled to or integrated with the proximal end 58 of the catheter adapter 54.

In some embodiments, the delivery device 10 may extend through the catheter system 80 in a similar way as illustrated in FIG. 5A-5D. For example, the transition portion 32 may be disposed within the lumen 60 of the catheter adapter 54 and/or within the catheter 55 when the catheter 12 is fully and/or partially advanced. As another example, the other transition portion 74 may be disposed within a lumen of the extension tubing 66 when the catheter 12 is fully and/or partially advanced. As yet another example, the distal end 40 of the guidewire 36 may be disposed distal to the distal tip 75 of the catheter 55 when the guidewire 36 is fully and/or partially advanced.

Figure 7A:
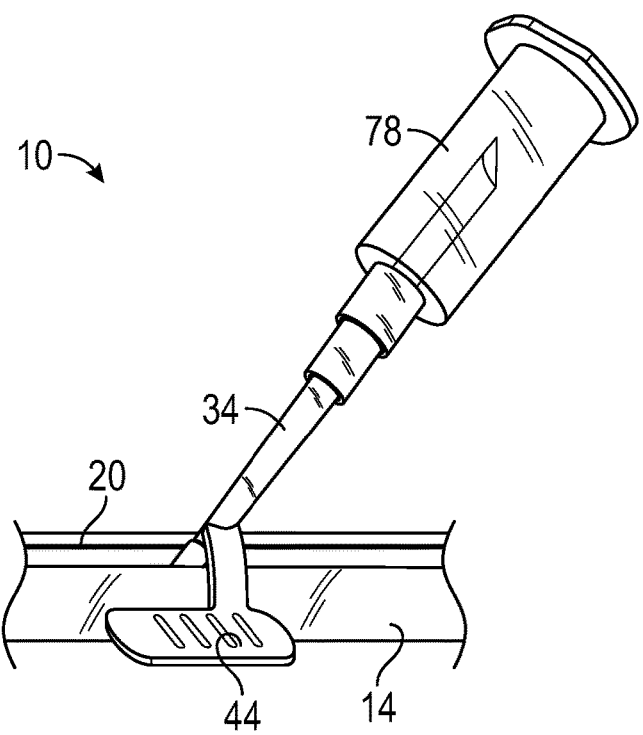
FIG. 7A is an upper perspective view of an example blood collection device, according to some embodiments.

Referring now to FIG. 7A, in some embodiments, the portion of the catheter hub 26 that extends through the slot 20 may be coupled to a blood collection device 78. In these and other embodiments, the delivery device 10 may or may not include the guidewire 36 and/or the guidewire hub 42. In some embodiments, the blood collection device 78 may include any suitable type of blood collection device. In some embodiments, the blood collection device 78 may include a reservoir. In some embodiments, the blood collection device 78 may include a vacuum tube, test tube, or syringe. In some embodiments, the blood collection device 78 may include an adapter, which may be configured to hold a test tube or syringe. In some embodiments, the blood collection device 78 may move distally as the catheter hub 26 is advanced and/or proximally as the catheter hub 26 is retracted.

Figure 7B:
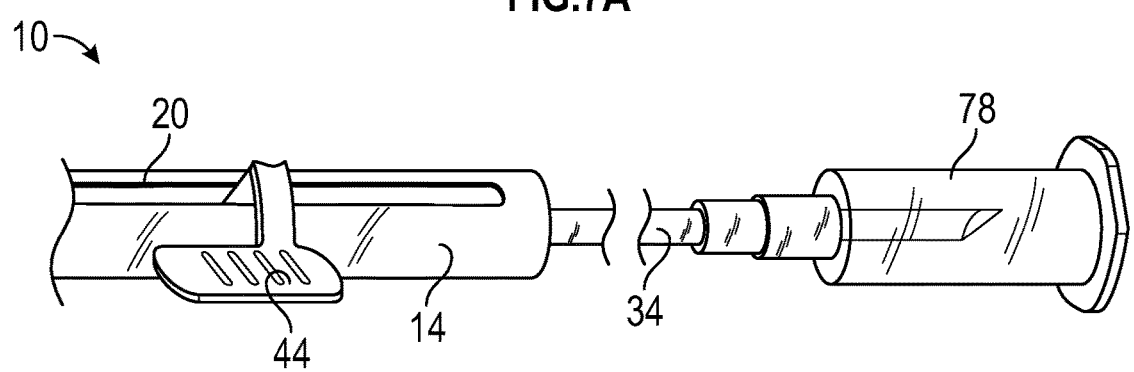
FIG. 7B is another upper perspective view of the blood collection device of FIG. 7A, according to some embodiments.

Referring now to FIG. 7B, in some embodiments, the catheter 12 may extend through an opening in the proximal end 18 of the housing 14, and the proximal end 18 of the catheter 12 may be coupled to the blood collection device 78. In some embodiments, the blood collection device 78 may move distally as the catheter hub 26 is moved distally and/or proximally as the catheter hub 26 moves proximally. In these and other embodiments, the delivery device 10 may or may not include the guidewire 36 and/or the guidewire hub 42.

In some embodiments, the blood collection device 78 may be used with the delivery device 10, which may be part of the catheter system 50 of FIG. 5 and/or the catheter system 80 of FIG. 6. In some embodiments, the blood collection device 78 may be configured to be used with the guidewire 36. For example, a proximal end of the guidewire 36 may extend parallel to and/or next to the extension tubing 34 such that the proximal end 38 of the guidewire 36 is disposed external to the extension tubing 34 and the blood collection device 78. In some embodiments, the delivery device 10 may not include the guidewire 36 and/or the guidewire hub 42. In some embodiments, the catheter 12 and/or the guidewire 36 may be replaced with another instrument, such as, for example, a probe, a light tube for disinfection, or another suitable instrument.

Figure 8:
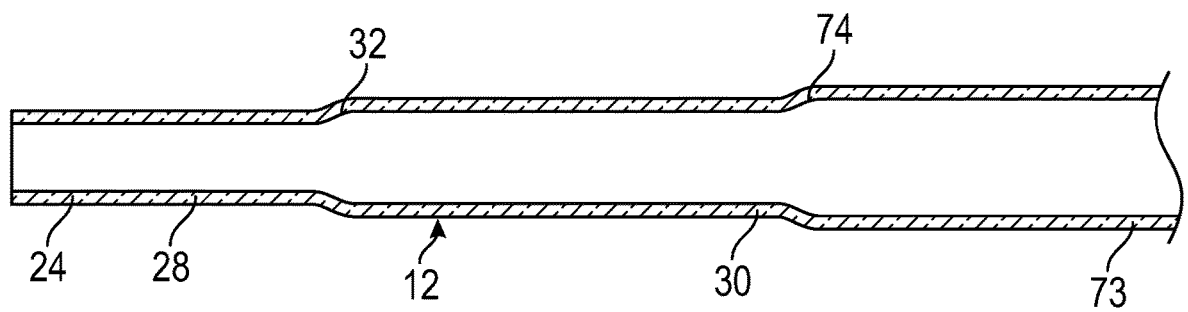
FIG. 8 is a cross-sectional view of another example catheter.

Referring now to FIG. 8, another example catheter 82 is illustrated, according to some embodiments. In some embodiments, the catheter 82 may include or correspond to the catheter 12 of any of the previous Figures. In some embodiments, the catheter 12 may include one or more features of the catheter 82. In some embodiments, the delivery device 10 may include the catheter 82 and/or the guide wire 36, and the delivery device 10 may be part of the catheter system 50 of FIG. 5 and/or the catheter system 80 of FIG. 6. In some embodiments, the transition portion 32 and/or the transition portion 74 may be tapered as illustrated, for example, in FIG. 8.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. An intravenous catheter system, comprising:
    a delivery device, comprising:
        a housing having a distal end, a proximal end, and a slot;
        a first catheter having a proximal end and a distal end; and
        a catheter hub disposed within the housing, wherein the first catheter is secured to the catheter hub, wherein a portion of the catheter hub extends through the slot and is moveable along the slot to advance the first catheter in a distal direction;
a catheter assembly, comprising:
   a catheter adapter having a distal end, a proximal end, a lumen extending between the distal end of the catheter adapter and the proximal end of the catheter adapter; and
   a second catheter secured to the catheter adapter and extending distally from the catheter adapter; and
an extension set coupled to the catheter adapter, comprising:
   an extension tube having a distal end and a proximal end; and
   a connector coupled to the proximal end of the extension tube, wherein the distal end of the first catheter is disposed beyond a distal end of the second catheter when the first catheter is advanced,
wherein the first catheter comprises a first portion, a second portion, and a transition portion disposed between the first portion and the second portion, wherein the first portion includes a first inner diameter along an entire length of the first portion and a first outer diameter along the entire length of the first portion, wherein the second portion is disposed proximal to the first portion, wherein the second portion includes a second inner diameter and a second outer diameter along an entire length of the second portion, wherein the second inner diameter is greater than the first inner diameter, wherein the second outer diameter is greater than the first outer diameter, wherein the transition portion is disposed within the lumen of the catheter adapter when the first catheter is advanced,
wherein the first catheter further comprises a third portion and a second transition portion disposed between the second portion and the third portion, wherein the third portion is disposed proximal to the second portion, wherein the third portion includes a third inner diameter along an entire length of the third portion and a third outer diameter along the entire length of the third portion, wherein the third inner diameter is greater than the second inner diameter, wherein the third outer diameter is greater than the second outer diameter, wherein the second transition portion is disposed within a lumen of the extension tube when the first catheter is advanced.

2. The intravenous catheter system of claim 1, wherein the catheter adapter further comprises a side port, wherein the extension tube extends from the side port.

3. The intravenous catheter system of claim 1, wherein the extension tube extends from the proximal end of the catheter adapter.

4. The intravenous catheter system of claim 1, further comprising:
   a guidewire having a proximal end and a distal end, wherein the guidewire is disposed within the first catheter; and
   a guidewire hub disposed within the housing proximal to the catheter hub, wherein the guidewire is secured to the guidewire hub, wherein a portion of the guidewire hub extends through the slot and is moveable along the slot to advance the guidewire in the distal direction, wherein the distal end of the guidewire is disposed distal to the distal end of the second catheter when the guidewire is advanced.

5. The intravenous catheter system of claim 4, wherein the guidewire is configured to be retracted when the first catheter is advanced.

* * * * *